United States Patent
Marotta et al.

(10) Patent No.: US 8,562,960 B2
(45) Date of Patent: Oct. 22, 2013

(54) COSMETIC COMPOSITION CONTAINING A POLYMER BLEND

(75) Inventors: Paul Henry Marotta, Farmingdale, NY (US); Katie Ann Frampton, West Babylon, NY (US); Tatyana R. Tabakman, Brooklyn, NY (US); John R. Castro, Hauppauge, NY (US); Elizabeth Martin, Stamford, CT (US)

(73) Assignee: ELC Management, LLC, New York, NY (US)

( * ) Notice: Subject to any disclaimer, the term of this patent is extended or adjusted under 35 U.S.C. 154(b) by 0 days.

(21) Appl. No.: 13/301,029

(22) Filed: Nov. 21, 2011

(65) Prior Publication Data

US 2012/0301416 A1 Nov. 29, 2012

Related U.S. Application Data

(63) Continuation-in-part of application No. 11/830,340, filed on Jul. 30, 2007, now abandoned.

(51) Int. Cl.
- *A61Q 1/10* (2006.01)
- *A61K 8/92* (2006.01)
- *A61K 8/81* (2006.01)

(52) U.S. Cl.
USPC .................. 424/70.7; 514/772.86; 514/772.5

(58) Field of Classification Search
USPC ....................................................... 424/70.16
See application file for complete search history.

(56) References Cited

U.S. PATENT DOCUMENTS

| | | | |
|---|---|---|---|
| 4,988,502 A * | 1/1991 | Ounanian et al. ................ 424/63 |
| 5,003,004 A | 3/1991 | Simms |
| 5,731,377 A | 3/1998 | Friel |
| 5,858,338 A | 1/1999 | Piot et al. |
| 6,126,929 A | 10/2000 | Mougin |
| 6,264,933 B1 | 7/2001 | Bodelin et al. |
| 6,375,941 B1 * | 4/2002 | Piot et al. ...................... 424/70.7 |
| 6,503,495 B1 | 1/2003 | Alwattari et al. |
| 6,793,940 B2 | 9/2004 | Tournilhac et al. |
| 6,946,123 B2 | 9/2005 | De La Polerie et al. |
| 2003/0235553 A1 * | 12/2003 | Lu et al. ................... 424/70.122 |
| 2004/0022752 A1 | 2/2004 | De La Polerie |
| 2004/0223933 A1 | 11/2004 | Hiwatashi et al. |
| 2004/0258648 A1 * | 12/2004 | Creamer et al. ........... 424/70.16 |
| 2005/0142154 A1 | 6/2005 | Blatt et al. |
| 2005/0163730 A1 | 7/2005 | Rosevear et al. |
| 2005/0175563 A1 * | 8/2005 | McNamara et al. ......... 424/70.1 |
| 2005/0239670 A1 * | 10/2005 | Stella et al. ................... 510/130 |
| 2006/0093568 A1 | 5/2006 | Blin et al. |
| 2006/0257342 A1 | 11/2006 | Mu et al. |
| 2007/0025943 A1 | 2/2007 | Patel |
| 2007/0142521 A1 | 6/2007 | Brahms et al. |

FOREIGN PATENT DOCUMENTS

FR 2834458 * 7/2003 ................... 424/401

OTHER PUBLICATIONS

PCT International Search Report; International Application No. PCT/US08/070957; Completion Date: Jan. 29, 2009; Date of Mailing: Jan. 29, 2009.
PCT Written Opinion of the International Searching Authority, or The Declaration; International Application No. PCT/US08/070957; Completion Date: Jan. 29, 2009; Mailing Date: Jan. 29, 2009.

* cited by examiner

*Primary Examiner* — Richard Schnizer
*Assistant Examiner* — Audrea Buckley
(74) *Attorney, Agent, or Firm* — Cynthia R. Miller

(57) ABSTRACT

The present invention relates to a cosmetic composition containing a unique polymer blend, which includes: (a) a first polymeric film-former having a first glass transition temperature ranging from about −20° C. to about 0° C.; (b) a second polymeric film-former having a second glass transition temperature that is at least 50° C. higher than the first glass transition temperature; and (c) a third cross-linked polymeric film-former. The cosmetic composition of the present invention can be applied to human skin or keratinous fibers for forming a film thereon with exceptionally long wearability, reduced flaking and smudge properties, and good removability by warm water.

17 Claims, No Drawings

COSMETIC COMPOSITION CONTAINING A POLYMER BLEND

CROSS-REFERENCE TO RELATED APPLICATIONS

The present application is a continuation-in-part of U.S. Ser. No. 11/830,340, filed on Jul. 30, 2007 now abandoned.

FIELD OF THE INVENTION

The present invention relates to a cosmetic composition suitable for application to human skin or keratinous fibers, more preferably to eyelashes. The cosmetic composition of the present invention contains a unique polymer blend and can be used to form a polymeric film having exceptional long-wear, reduced flaking and smudging properties, and good removability by warm water.

BACKGROUND OF THE INVENTION

Eye make-up products, such as eyeliners and mascaras, constitute a significant share of the cosmetics market. Eyeliners are applied along the user's eyelids to enhance and emphasize the contour of the user's eyes, and mascaras, by forming a colored coating over the user's eyelashes, function to darken, and in some incidents can even volumize/extend/curl, the user's eyelashes.

In spite of their initial beauty-enhancing characteristics, most conventional eye make-up compositions have failed to produce the desired beautifying effects after long hours of wearing. Problems such as flaking and smudging are well known for eye make-up compositions. On the other hand, the so-called water-proof and long-wear eye make-up compositions, which typically include one or more water-insoluble latex polymers, are extremely hard to remove. Special eye make-up removers are required, which contain oils or organic solvents that leave an oily or greasy film on the skin after application. For users with relatively sensitive eyes, the special eye mark-up removers may even cause irritation or allergic reactions.

There is therefore a continuing need for improved eye make-up compositions. It will be especially advantageous to provide a cosmetic composition that not only has the long-wear and reduced flaking and smudging properties, but can also readily be removed by using merely warm water.

SUMMARY OF THE INVENTION

In one aspect, the present invention relates to a cosmetic composition suitable for application to human skin or keratinous fibers, comprising:
 (a) a first polymeric film-former having a first glass transition temperature ranging from about −20° C. to about 0° C.;
 (b) a second polymeric film-former having a second glass transition temperature that is at least 50° C. higher than the first glass transition temperature; and
 (c) a third cross-linked polymeric film-former;
wherein the first polymeric film-former and the second polymeric film former are present in the composition in a ratio in the range of from about 2:1 to about 26:1, said ratio based on the total weight of the first and second polymeric film formers in the composition.

Preferably, the first polymeric film-former comprises one or more water-soluble or water-dispersible acrylates copolymers containing one or more monomers selected from the group consisting of $C_1$-$C_8$ alkyl acrylates, $C_1$-$C_8$ alkyl methacrylates, $C_1$-$C_4$ alkoxy acrylates, $C_1$-$C_4$ alkoxy methacrylates, and combinations thereof. As a non-limiting, illustrative example, the first polymeric film-former may comprise an acrylates/octyl acrylate copolymer, which can be provided in an amount ranging from about 5% to about 15%, and more preferably from about 7.5% to about 10%, by total weight of the cosmetic composition. The first polymeric film-former may further comprise an ethyl acrylate/methyl methacrylate/methacrylic acid copolymer, which can be provided in an amount ranging from about 0.1% to about 5%, and more preferably from about 1% to about 3%, by total weight of the cosmetic composition. Therefore, the first polymeric film-former, including optional ethyl acrylate/methyl methacrylate/methacrylic acid copolymer, may be present in the compositions in the range of from about 5.0% to about 20%, more preferably in the range of from about 7.5% to about 13%, by total weight of the compositions.

The second polymeric film-former preferably comprises one or more acrylates copolymers having one or more monomers selected from the group consisting of acrylates, alkyl acrylates, methacrylates, alkyl methacrylates, hydroxyesters acrylates, and combinations thereof. As a non-limiting, illustrative example, the second polymeric film-former may comprise an acrylates/hydroxyesters acrylates copolymer, which can be provided in an amount ranging from about 0.05% to about 2%, and more preferably from about 0.5% to about 1%, by total weight of said cosmetic composition. The second polymeric film-former may also comprise a mixture of one or more acrylates copolymers and one or more vinyl polymers, such as polyvinyl acetate (PVAc). The PVAc may be provided in an amount ranging, for example, from about 0.1% to about 5%, and more preferably from about 1% to about 3%, by total weight of said cosmetic composition. Therefore, the second polymeric film-former, including optional vinyl polymer, may be present in the compositions in an amount in the range of from about 0.05% to about 7%, more preferably in the range of from about 0.5% to about 4.0% by total weight of the cosmetic composition.

The third cross-linked polymeric film-former may comprise any suitable crosspolymer that is at least partially cross-linked by covalent or ionic bonds to form a polymeric network, which function to enhance the compatibility between the first and second polymeric film-formers of different glass transition temperatures and avoid potential macro-phase separation. As a non-limiting, illustrative example, the third cross-linked polymeric film-former may comprise a taurate crosspolymer, which preferably, but not necessarily, contains acryloyl dimethyl taurate monomers and one or more additional monomers selected from the group consisting of styrene, acrylic acid, methacrylic acid, vinyl chloride, vinyl acetate, vinyl pyrrolidone, isoprene, vinyl alcohol, vinyl methylether, chloro-styrene, dialkylamino-styrene, maleic acid, acrylamide, methacrylamide, and combinations thereof. More preferably, the taurate crosspolymer is an acryloyl dimethyltaurate/vinyl pyrrolidone crosspolymer or an acryloyl dimethyltaurate/beheneth-25 methacrylate crosspolymer. As another non-limiting, illustrative example, the third cross-linked polymeric film-former may comprise an acryates/$C_{10}$-$C_{30}$ alkyl acrylate crosspolymer, which is preferably cross-linked by a cross-linking agent selected from the group consisting of allyl ether of sucrose and allyl ether of pentaerythritol. The above-described third cross-linked polymeric film-former is preferably provided in an amount ranging, for example, from about 0.01% to about 2%, and more preferably from about 0.1% to about 1%, by total weight of said cosmetic composition.

The above-described cosmetic composition preferably, but not necessarily, comprises an oil-in-water emulsion. More preferably, the first polymeric film-former, the second polymeric film-former, and the third cross-linked polymeric film former are dispersed in an aqueous phase of said oil-in-water emulsion. Such cosmetic composition may further comprise one or more waxes in an oil phase of the oil-in-water emulsion.

In another aspect, the present invention relates to a cosmetic composition comprising:

(a) from about 7.5 wt % to about 10 wt % of an acrylates/octyl acrylate copolymer;
(b) from about 1.0 wt % to about 3 wt % of an ethyl acrylate/methyl methacrylate/methacrylic acid copolymer;
(c) from about 0.5 wt % to about 1 wt % of an acrylates/hydroxyesters acrylates copolymer;
(d) from about 1 wt % to about 3 wt % of polyvinyl acetate; and
(e) from about 0.1 wt % to about 1 wt % of a cross-linked polymeric film-former selected from the group consisting of a taurate crosspolymer or an acrylates/$C_{10}$-$C_{30}$ alkyl acrylate crosspolymer.

Other aspects and objectives of the present invention will become more apparent from the ensuing description, examples, and claims.

DETAILED DESCRIPTION OF THE INVENTION AND PREFERRED EMBODIMENTS THEREOF

Except in operating and comparative examples, or where otherwise explicitly indicated, all numbers in this description indicating amounts or ratios of material or conditions of reaction, physical properties of materials and/or use are to be understood as modified by the word "about." All amounts are presented as percentages by weight of the final composition, unless otherwise specified.

The cosmetic compositions of the present invention comprise the following basic elements: (a) a first polymeric film-former having a first glass transition temperature ranging from about −20° C. to about 0° C.; (b) a second polymeric film-former having a second glass transition temperature that is at least 50° C. higher than the first glass transition temperature; and (c) a third cross-linked polymeric film-former. Although not wishing to be bound by any particular theory, it is believed by the inventors that the second polymeric film-former of relatively high glass transition temperature functions to impart long wear, reduced flaking and smudging properties to the polymeric film formed by the cosmetic composition of the present invention, while the first polymeric film-former of relatively low glass transition temperature is capable of melting upon contact with warm water and thereby allows the polymeric film so formed to be easily removed by warm water, without any special oil- or organic solvent-based make-up remover. Typically, when two or more polymeric film-formers of significantly different glass transition temperatures are blended together, the resulting blend is likely to suffer from poor film-forming performance, due to macro-phase separation caused by the incompatibility between such polymeric film-formers. In order to solve this problem, the present invention provides a third cross-linked polymeric film-former, which forms a polymeric network to improve binding between the first and second film formers, avoid potential macro-phase separation, and ultimately improve the film-forming performance of the resulting film. Consequently, the resulting film is a continuous, flexible, and stable polymeric film with long-wear characteristics, reduced flaking and smudging properties, and sufficient removability by warm water.

Suitable polymers that can be used as the first polymeric film-former of relatively low glass transition temperature include, but are not limited to, water-soluble or water-dispersible acrylates copolymers. Preferably, the water-soluble or water-dispersible acrylates copolymers as used in the present invention contain one or more monomers selected from the group consisting of $C_1$-$C_8$ alkyl acrylates, $C_1$-$C_8$ alkyl methacrylates, $C_1$-$C_4$ alkoxy acrylates, $C_1$-$C_4$ alkoxy methacrylates, and combinations thereof. More preferably, the monomers are selected from the group consisting of methyl acrylate, methoxy acrylate, methyl methacrylate, methoxy methacrylate, ethyl acrylate, ethoxy acrylate, ethyl methacrylate, ethoxy methacrylate, propyl acrylate, propyl oxide acrylate, propyl methacrylate, propyl oxide methacrylate, isopropyl acrylate, isopropyl oxide acrylate, isopropyl methacrylate, isopropyl oxide methacrylate, butyl acrylate, butyl oxide acrylate, butyl methacrylate, butyl oxide methacrylate, isobutyl acrylate, isobutyl oxide acrylate, isobutyl methacrylate, isobutyl oxide methacrylate, tertiary butyl acrylate, tertiary butyl oxide acrylate, tertiary butyl methacrylate, tertiary butyl oxide methacrylate, pentyl acrylate, pentyl methacrylate, isopentyl acrylate, isopentyl methacrylate, neopentyl acrylate, neopentyl methacrylate, hexyl acrylate, hexyl methacrylate, isohexyl acrylate, isohexyl methacrylate, heptyl acrylate, heptyl methacrylate, isoheptyl acrylate, isoheptyl methacrylate, octyl acrylate, octyl methacrylate, isooctyl acrylate, isooctyl methacrylate, 2-ethylhexyl acrylate, 2-ethylhexyl methacrylate, and combinations thereof.

For example, the first polymeric film-former may comprise an acrylates/octyl acrylate copolymer or an ethyl acrylate/methyl methacrylate copolymer. Such acrylates/octyl acrylate copolymer or ethyl acrylate/methyl methacrylate copolymer is commercially available in the form of aqueous dispersions under the trade name DAITOSOL® 5000SJ or DAITOSOL® 5000AD from Kobo Products, Inc. at South Plainfield, N.J. When an acrylates/octyl acrylate copolymer is used in the present invention, it is preferably provided in an amount of about 5-15 wt % (measured against the total weight of the final composition), and more preferably about 7.5-10 wt %. As an example, DAITOSOL® 5000SJ comprises 50% wt % acrylates/octyl acrylates copolymer dispersed in 49.7 wt % with 0.3 wt % laureth-20 (lauryl alcohol and oxirane). The first polymeric film-former may further comprise one or more additional water-soluble or water-dispersible acrylates copolymers, such as ethyl acrylate/methyl methacrylate/acrylic acid copolymers and ethyl acrylate/methyl methacrylate/methacrylic acid copolymers that are commercially available in the form of aqueous dispersions under the trade names Covacryl® A15, Covacryl® E14, and Covacryl® P12 from Sensient Cosmetic Technologies LCM USA at South Plainfield, N.J. As an example, Covacryl® P12 is an emulsion of 30 wt % acrylic copolymer dispersed in 70 wt % water. When an ethyl acrylate/methyl methacrylate/methacrylic acid copolymer is used in the present invention, it is preferably provided in an amount of about 0.1-5 wt % (measured against the total weight of the final composition), and more preferably about 1-3 wt %.

Suitable polymers that can be used in the present invention as the second polymeric film-former of relatively high glass transition temperature include, but are not limited to, acrylates copolymers having one or more monomers selected from the group consisting of acrylates, alkyl acrylates, methacrylates, alkyl methacrylates, hydroxyesters acrylates, and combinations thereof. Preferably, such acrylates copolymers contain hydroxyesters acrylate monomers and are characterized by limited water solubility or dispersibility. The second polymeric film-former may also include a polymer blend of one or more above-mentioned acrylates copolymers and one or more additional vinyl polymers, such as polyethylene (PE), polypropylene (PP), polybutadiene (PB), polystyrene (PS), polyvinyl chloride (PVC), polyvinyl acetate (PVAc), polyvinyl alcohol (PVA), and polyacrylonitrile. For example, the second polymeric film-former may include a mixture of an acrylates/hydroxyesters acrylates copolymer and polyvinyl acetate, which is commercially available from under the trade names THORCO FLEX IV C and THORCO FLEX-3 from Thornley Company at Wilmington, Del. As an example, THORCO FLEX IV C is a mixture of 31-35 wt % PVA and 14-16 wt % acrylates/hydroxyesters acrylates (HEA) copolymer dispersed in about 45 wt % water (with other additives, such as butylene glycol, hexylene glycol, caprylyl glycol, phenoxyethanol, and sodium laureth sulfate). The acrylates/hydroxyesters acrylates copolymer can be provided in an amount typically ranging from about 0.05 wt % to about 2 wt %, more preferably from about 0.5 wt % to about 1 wt %, and the polyvinyl acetate can be provided in an amount typically ranging from about 0.1 wt % to about 5 wt %, more preferably from about 1 wt % to about 3 wt %.

In accordance with certain preferred embodiments of the compositions of the present invention, the first polymeric film former, including acrylates/octyl acrylate copolymer or an ethyl acrylate/methyl methacrylate copolymer and optionally, ethyl acrylate/methyl methacrylate/methacrylic acid copolymer, is present in the compositions in a range of from about 7.5% to about 13%, and the second polymeric film former, including acrylates copolymers and optionally, vinyl polymer, is present in the compositions in a range of from about 0.5% to about 4%, by total weight of the compositions, corresponding to a ratio of the first polymeric film former to the second polymeric film former in the range of from about 2:1 to about 26:1.

The third cross-linked polymeric film-former as used in the present invention may be any suitable crosspolymer that is at least partially cross-linked by covalent or ionic bonds to form a polymeric network for enhancing the binding/compatibility between the first and second polymeric film-formers of different glass transition temperatures and avoid potential macro-phase separation. As a non-limiting, illustrative example, the third cross-linked polymeric film-former may comprise a taurate crosspolymer, which preferably, but not necessarily, contains acryloyl dimethyl taurate monomers and one or more additional monomers selected from the group consisting of styrene, acrylic acid, methacrylic acid, vinyl chloride, vinyl acetate, vinyl pyrrolidone, isoprene, vinyl alcohol, vinyl methylether, chloro-styrene, dialkylamino-styrene, maleic acid, acrylamide, methacrylamide, and combinations thereof. More preferably, the taurate crosspolymer is an acryloyl dimethyltaurate/vinyl pyrrolidone crosspolymer or an acryloyl dimethyltaurate/beheneth-25 methacrylate crosspolymer, which is commercially available under the tradename of Aristoflex® AVC, AVL, or HMB from Clariant Corporation at Charlotte, N.C. As another non-limiting, illustrative example, the third cross-linked polymeric film-former may comprise an acrylates/$C_{10}$-$C_{30}$ alkyl acrylate crosspolymer, which is preferably cross-linked by a cross-linking agent selected from the group consisting of allyl ether of sucrose and allyl ether of pentaerythritol. Such acrylates/$C_{10}$-$C_{30}$ alkyl acrylate crosspolymers are commercially available from Noveon, Inc. at Cleveland, Ohio. The above-described third cross-linked polymeric film-former is preferably provided in an amount ranging, for example, from about 0.01% to about 2%, and more preferably from about 0.1% to about 1%, by total weight of the cosmetic composition.

The cosmetic compositions of the present invention may be formulated as a single aqueous phase, a single oil phase, a water-in-oil emulsion, an oil-in-water emulsion, or an emulsion with three or more phases. Preferably, the cosmetic composition comprises an oil-in-water emulsion with the above-described polymeric components dispersed in an aqueous phase therein. More preferably, the oil-in-water emulsion comprises one or more gelling or structuring agents in an oil phase therein.

For example, the compositions may include one or more waxy materials such as candelilla, carnauba waxes, beeswax, spermaceti, carnauba, baysberry, montan, ozokerite, ceresin, paraffin, synthetic waxes such as Fisher-Tropsch waxes, silicone waxes (e.g., DC 2503 from Dow Corning), microcrystalline waxes and the like; soaps, such as the sodium and potassium salts of higher fatty acids, i.e., acids having from 12 to 22 carbon atoms; amides of higher fatty acids; higher fatty acid amides of alkylolamines; dibenzaldehyde-monosorbitol acetals; alkali metal and alkaline earth metal salts of the acetates, propionates and lactates; and mixtures thereof. Also useful are polymeric materials such as, locust bean gum, sodium alginate, sodium caseinate, egg albumin, gelatin agar, carrageenin gum sodium alginate, xanthan gum, quince seed extract, tragacanth gum, starch, chemically modified starches and the like, semi-synthetic polymeric materials such as cellulose ethers (e.g. hydroxyethyl cellulose, methyl cellulose, hydroxypropyl cellulose, carboxymethyl cellulose, hydroxy propylmethyl cellulose), polyvinylpyrrolidone, polyvinylalcohol, guar gum, hydroxypropyl guar gum, soluble starch, cationic celluloses, cationic guars and the like and synthetic polymeric materials such as carboxyvinyl polymers, polyvinylpyrrolidone, polyvinyl alcohol polyacrylic acid polymers, polymethacrylic acid polymers, polyvinyl acetate polymers, polyvinyl chloride polymers, polyvinylidene chloride polymers and the like. Inorganic thickeners may also be used such as aluminum silicates, such as, for example, bentonites, or a mixture of polyethylene glycol and polyethylene glycol stearate or distearate.

Also useful herein are hydrophilic gelling agents such as the acrylic acid/ethyl acrylate copolymers and the carboxyvinyl polymers sold by the B.F. Goodrich Company under the trademark of Carbopol® resins. These resins consist essentially of a colloidally water-soluble polyalkenyl polyether crosslinked polymer of acrylic acid crosslinked with from 0.75% to 2.00% of a crosslinking agent such as polyallyl sucrose or polyallyl pentaerythritol. Examples include Carbopol 934, Carbopol 940, Carbopol 950, Carbopol 980, Carbopol 951 and Carbopol 981. Carbopol 934 is a water-soluble polymer of acrylic acid crosslinked with about 1% of a polyallyl ether of sucrose having an average of about 5.8 allyl groups for each sucrose molecule. Also suitable for use herein are carbomers sold under the Trade Name "Carbopol Ultrez 10, Carbopol ETD2020, Carbopol 1382, Carbopol 1342 and Pemulen TR-1 (CTFA Designation: Acrylates/10-30 Alkyl Acrylate Crosspolymer). Combinations of the above polymers are also useful herein. Other gelling agents suitable for use herein include oleogels such as trihydroxystearin. Hydrophobically modified celluloses are also suitable for use herein.

The compositions hereof, and especially the emulsions hereof, may contain a structuring agent. Structuring agents are particularly preferred in the oil-in-water emulsions of the present invention. Without being limited by any particular theory, it is believed that the structuring agent assists in providing rheological characteristics to the composition which contribute to the stability of the composition. For example, the structuring agent tends to assist in the formation of the liquid crystalline gel network structures. The structuring agent may also function as an emulsifier or surfactant. Preferred compositions of this invention contain from about 0.1% to about 20%, more preferably from about 0.1% to about 10%, still more preferably from about 0.5% to about 9%, of one or more structuring agents. Preferred structuring agents are those having an HLB of from about 1 to about 8 and having a melting point of at least about 45° C. Suitable structuring agents are those selected from saturated $C_{14}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, $C_{14}$ to $C_{30}$ hydroxylated and nonhydroxylated saturated fatty acids, $C_{14}$ to $C_{30}$ saturated ethoxylated fatty acids, amines and alcohols containing from about 1 to about 5 moles of ethylene oxide diols, $C_{14}$ to $C_{30}$ saturated glyceryl mono esters with a monoglyceride content of at least 40%, $C_{14}$ to $C_{30}$ saturated polyglycerol esters having from about 1 to about 3 alkyl group and from about 2 to about 3 saturated glycerol units, $C_{14}$ to $C_{30}$ glyceryl mono ethers, $C_{14}$ to $C_{30}$ sorbitan mono/diesters, $C_{14}$ to $C_{30}$ saturated ethoxylated sorbitan mono/diesters with about 1 to about 5 moles of ethylene oxide, $C_{14}$ to $C_{30}$ saturated methyl glucoside esters, $C_{14}$ to $C_{30}$ saturated sucrose mono/diesters, $C_{14}$ to $C_{30}$ saturated ethoxylated methyl glucoside esters with about 1 to about 5 moles of ethylene oxide, $C_{14}$ to $C_{30}$ saturated polyglucosides having an average of between 1 to 2 glucose units and mixtures thereof, having a melting point of at least about 45° C.

The preferred structuring agents of the present invention are selected from stearic acid, palmitic acid, stearyl alcohol, cetyl alcohol, behenyl alcohol, stearic acid, palmitic acid, the polyethylene glycol ether of stearyl alcohol having an average of about 1 to about 5 ethylene oxide units, the polyethylene glycol ether of cetyl alcohol having an average of about 1 to about 5 ethylene oxide units, and mixtures thereof. More preferred structuring agents of the present invention are selected from stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof. Even more preferred structuring agents are selected from stearic acid, palmitic acid, stearyl alcohol, cetyl alcohol, behenyl alcohol, steareth-2, and mixtures thereof.

The cosmetic compositions of the present invention typically contain one or more inorganic or organic pigments. There are no specific limitations as to the pigment or colorant. Specific examples are talc, mica, magnesium carbonate, calcium carbonate, magnesium silicate, aluminum magnesium silicate, silica, titanium dioxide, zinc oxide, red iron oxide, yellow iron oxide, black iron oxide, ultramarine, polyethylene powder, methacrylate powder, polystyrene powder, silk powder, crystalline cellulose, starch, titanated mica, iron oxide titanated mica, bismuth oxychloride, and the like. In a preferred, but not necessary, embodiment of the present invention, metallic oxide pigments, such as titanium, zinc, cerium or zirconium oxides, are used at a concentration of between 0.1 and 15%, and in particular between 0.5 and 10% by total weight of the composition. These pigments are preferably used in the form of nanopigments with a mean diameter of loan than 100 nm, generally of between 5 and 50 nm. These nanopigments may be optionally coated. The pigments or colorants used in the present invention may also be selected from aluminum, barium or calcium salts or lakes. Other colors, such as organic or synthetic dyes, can also be included in the cosmetic compositions of the present invention.

Additional fillers include, but are not limited to, inorganic powders or particulates such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powders or particulates such as polyamide resin powder (nylon powder), polyamide resin fiber (nylon fiber), cyclodextrin, methyl polymethacrylate powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as magnesium oxide. These pigments and powders can be used either independently or in combination.

Additional substances which may be formulated into the cosmetic composition of the present application include, but are not limited to: moisturizing agents, astringent agents, chelating agents, surfactants, emollients, preservatives, stabilizers, humectants, pigments, and the like.

For example, a variety of water soluble preservatives can be added to the cosmetic compositions of the present invention to provide a prolonged shelf life. Suitable preservatives include, but are not limited to: potassium sorbate, imidazolidinyl urea, p-hydroxy benzoate, esters of p-hydroxybenzoic acid, CTFA designation parabens, ethylhexylglycerin, caprylyl glycol/phenoxyethanol/hexylene glycol, and the like. Other preservatives suitable for use in the cosmetic compositions of the present invention are disclosed in the International Cosmetic Ingredient Dictionary and Handbook, twelfth edition, 2004, the entire disclosure of which is herein incorporated by reference.

Humectants which may be used include, but are not limited to: polyhydric alcohols including glycerol, polyalkylene glycols, and alkylene polyols and mixtures thereof, hyaluronic acid, urea, glycerin, sorbitol, sodium 2-pyrrolidone-5-carboxylate, soluble collagen, dibutylphthalate and gelatin.

The cosmetic composition of the present invention may optionally comprise a fragrance in an amount sufficient to make the composition more appealing to the consumer. Preferably, the fragrance is in the amount of from about 0.01% to about 10% by total weight of the composition.

The following examples further illustrate various specific embodiments of the present invention, without limiting the broad scope thereof.

EXAMPLE 1

Mascara Compositions

FORMULA I

| Phases | Components | Wt % |
|---|---|---|
| Phase 1 | Deionized Water | 15.00 |
| | Panthenol | 0.01 |
| | Disodium EDTA | 0.10 |
| | Butylene Alcohol | 0.50 |
| | Hexylene Glycol | 1.00 |
| | Ammonium Acryloyldimethyltaurate/Beheneth-25 Methacrylate Crosspolymer | 0.20 |
| Phase 2 | Deionized Water | 15.59 |
| | Polyvinyl Alcohol | 0.10 |
| | Simethicone | 0.08 |
| | Iron Oxides (Black) | 7.00 |
| | Tromethamine | 1.00 |
| | Ammonium Hydroxide | 0.01 |
| | Isostearic Acid | 0.10 |
| | Bentonite | 0.05 |
| Phase 3 | Bentonite | 1.00 |
| | Kaolin | 2.00 |
| | Silica | 4.25 |
| | Mica | 4.00 |
| Phase 4 | PEG-100 Stearate | 0.60 |
| | Glyceryl Stearate | 1.25 |
| | Stearic Acid | 2.70 |
| | Isostearic Acid | 0.71 |
| | Carnauba Wax | 2.50 |
| | Beeswax | 3.70 |
| | Sucrose Distearate | 0.70 |
| | Cholesterol | 0.10 |
| | Macadamia Nut Oil | 0.10 |
| Phase 5 | Dimethicone | 1.00 |
| Phase 6 | Deionized Water | 0.90 |
| | Tromethamine | 0.15 |
| Phase 7 | Thorco-Flex ® IV C (45% Water/31-35% Polyvinyl Acetate/14-16% Acrylates//Hydroxyesters Acrylates Copolymer/Butylene Glycol) | 5.00 |
| Phase 8 | Covacryl ® P12 (70% Water/30% Acrylates Copolymer) | 5.00 |
| Phase 9 | Deionized Water | 1.00 |
| | Tromethamine | 0.30 |
| Phase 10 | Daitosol ® 5000SJ (49.7% Water/0.3% laureth-20/50% Acrylates//Octyl Acrylate Copolymer) | 17.00 |
| Phase 11 | Jeecide ® CAP-5 (Phenoxyethanol/Caprylyl Glycol/Potassium Sorbate/Water/Hexylene Glycol) | 0.70 |
| | Ethylhexyl Glycerin | 0.60 |
| | Green Tea Extract | 1.00 |
| | Cosmocil ® CQ (Water/Polyaminopropyl Biguanide) | 0.05 |
| Phase 12 | Alcohol Denatured | 2.50 |

FORMULA II

| Phases | Components | Wt % |
|---|---|---|
| Phase 1 | Deionized Water | 10.00 |
| | Disodium EDTA | 0.10 |
| | Butylene Alcohol | 0.50 |
| | Hexylene Glycol | 1.00 |
| | Ammonium Acryloyldimethyltaurate/Beheneth-25 Methacrylate Crosspolymer | 0.20 |
| Phase 2 | Deionized Water | 20.81 |
| | Polyvinyl Alcohol | 0.10 |
| | Simethicone | 0.08 |
| | Iron Oxides (Black) | 7.00 |
| | Tromethamine | 1.00 |
| | Isostearic Acid | 0.10 |
| | Bentonite | 0.05 |
| Phase 3 | Bentonite | 1.00 |
| Phase 4 | Kaolin | 2.00 |
| | Silica | 4.25 |
| Phase 5 | PEG-100 Stearate | 0.60 |
| | Glyceryl Stearate | 1.25 |
| | Stearic Acid | 2.70 |
| | Isostearic Acid | 0.71 |
| | Carnauba Wax | 2.50 |
| | Beeswax | 3.70 |
| | Sucrose Distearate | 0.70 |
| Phase 6 | Dimethicone | 1.00 |
| Phase 7 | Deionized Water | 0.90 |
| | Tromethamine | 0.15 |
| | Thorco-Flex ® IV C (45% Water/31-35% Polyvinyl Acetate/14-16% Acrylates//Hydroxyesters Acrylates Copolymer/Butylene Glycol) | 5.00 |
| Phase 8 | Covacryl ® P12 (70% Water/30% Acrylates Copolymer) | 5.00 |
| Phase 9 | Deionized Water | 1.00 |
| | Tromethamine | 0.30 |
| | Daitosol ® 5000SJ (49.7% Water/0.3% laureth-20/50% Acrylates//Octyl Acrylate Copolymer) | 17.00 |
| | Mica | 4.00 |
| Phase 10 | Jeecide ® CAP-5 (Phenoxyethanol/Caprylyl Glycol/Potassium Sorbate/Water/Hexylene Glycol) | 0.70 |
| | Ethylhexyl Glycerin | 0.60 |
| | Green Tea Extract | 1.00 |
| | Cosmocil ® CQ (Water/Polyaminopropyl Biguanide) | 0.05 |
| Phase 11 | Alcohol Denatured | 2.50 |

FORMULA III

| Phases | Components | Wt % |
|---|---|---|
| Phase 1 | Deionized Water | 10.873 |
| | Disodium EDTA | 0.100 |
| | Bentonite | 1.500 |
| | Butylene Glycol | 0.500 |
| Phase 2 | Deionized Water | 10.000 |
| | Iron Oxides (Black) | 7.000 |
| | Simethicone | 0.080 |
| Phase 3 | Deionized Water | 6.000 |
| | Polyvinyl Alcohol | 1.500 |
| Phase 4 | Hexylene Glycol | 1.000 |
| Phase 5 | Kaolin | 2.000 |
| | Silica | 4.250 |
| | Mica | 4.000 |
| Phase 6 | PEG-100 Stearate | 0.600 |
| | Glyceryl Stearate | 1.250 |
| | Stearic Acid | 0.900 |
| | Isostearic Acid | 2.700 |
| | Carnauba Wax | 2.500 |
| | Beeswax | 3.700 |
| | Ganex ® V-216 (PVP/Hexadecene Copolymer) | 1.000 |
| | Rapeseed Seed Oil | 1.000 |
| | Sucrose Distearate | 0.700 |
| Phase 7 | Deionized Water | 1.000 |
| | Ammonium Hydroxide | 0.600 |
| Phase 8 | Dimethicone | 1.000 |
| Phase 9 | Ammonium Acryloyldimethyltaurate/Beheneth-25 Methacrylate Crosspolymer | 0.300 |
| Phase 10 | Deionized Water | 1.000 |
| | Ammonium Hydroxide | 0.020 |
| | Thorco-Flex ® IV C (45% Water/31-35% Polyvinyl Acetate/14-16% Acrylates//Hydroxyesters Acrylates Copolymer/Butylene Glycol) | 5.000 |

-continued

FORMULA III

| Phases | Components | Wt % |
|---|---|---|
| Phase 11 | Covacryl ® P12 (70% Water/30% Acrylates Copolymer) | 5.000 |
| Phase 12 | Deionized Water | 1.000 |
| | Ammonium Hydroxide | 0.077 |
| | Daitosol ® 5000SJ (49.7% Water/0.3% laureth-20/50% Acrylates//Octyl Acrylate Copolymer) | 17.000 |
| Phase 13 | Jeecide ® CAP-5 (Phenoxyethanol/Caprylyl Glycol/Potassium Sorbate/Water/Hexylene Glycol) | 0.700 |
| | Ethylhexyl Glycerin | 0.600 |
| | Green Tea Extract | 1.000 |
| | Cosmocil ® CQ (Water/Polyaminopropyl Biguanide) | 0.050 |
| Phase 14 | Alcohol Denatured | 2.500 |

EXAMPLE 2

Product Performance Tests

Various tests were carried out in order to evaluate the product performance of two mascara compositions I and II, which were respectively formulated according to Formulas I and II hereinabove. The tests were conducted by an expert panel composed of 10 women, and covered the following aspects of product performance with respect to mascara:

A. Flaking

The term "flaking" as used herein refers to the phenomenon of having pieces of mascara or other eye makeup product falling onto skin around the eyes or in the eye after defined hours. Specifically, the panelists were asked to evaluate the degree of flaking 8 hours after the application of the mascara product. The grades assigned for each panelist ranged from 0 to 10, with 0 being no flaking at all, and 10 being extreme flaking B. Smudging The term "smudging" as used herein refers to the phenomenon of mascara or other eye makeup product mixing with moisture or oil on the surface of the skin and smearing/spreading into adjacent skin surfaces (particularly in the under-eye area) after defined hours. Specifically, the panelists were asked to evaluate the degree of smudging 8 hours after the application of the mascara product. The grades assigned for each panelist ranged from 0 to 10, with 0 being no smudging at all, and 10 being extreme smudging.

C. Wear

The term "wear" as used herein refers to the reduction in visibility or intensity of mascara or other eye makeup product after defined hours, as compared to that after immediate application. Note that the term "long wear" as used in the present invention refers to the lack of reduction in visibility or intensity of mascara or other eye makeup product after extended hours. Specifically, the panelists were asked to evaluate the degree of wear 8 hours after the application of the mascara product. The grades assigned for each panelist ranged from 0 to 10, with 0 being no wear at all (i.e., no reduction in visibility or intensity after 8 hours in comparison with that after immediate application), and 10 being extreme wear (i.e., extreme reduction in visibility or intensity after 8 hours in comparison with that after immediate application).

D. Ease of Removal by Warm Water

The term "ease of removal using warm water" or "warm water removability" as used herein refers to the amount of mascara or other eye makeup product that can be removed by splashing the eye area three (3) times with warm water having an elevated temperature of about 35° C., followed by gently wiping the eye area with a cotton pad. Specifically, the panelists were asked to evaluate the ease of removal by warm water 8 hours after application of the mascara product. The grades assigned for each panelist ranged from 0 to 10, with 0 being complete removal (i.e., no trace of mascara residue on the lashes), and 10 being no removal at all (i.e., no trace of mascara residue on the cotton pad).

The average grades obtained from the above tests were listed as follows:

| | Flaking | Smudging | Wear | Ease of Removal by Warm Water |
|---|---|---|---|---|
| Mascara I | 0.9 | 0.5 | 1.1 | 5.1 |
| Mascara II | 0.7 | 0.6 | 1.0 | 5.5 |

Although the invention has been variously disclosed herein with reference to illustrative embodiments and features, it will be appreciated that the embodiments and features described hereinabove are not intended to limit the scope of the invention, and that other variations, modifications and other embodiments will suggest themselves to those of ordinary skill in the art. The invention therefore is to be broadly construed, consistent with the claims hereafter set forth.

What is claimed is:

1. A mascara or eyeliner composition comprising:
   (a) a first polymeric film-former having a first glass transition temperature ranging from about −20° C. to about 0° C., wherein the first polymeric film-former comprises one or more water-soluble or water-dispersible acrylates copolymers comprising one or more monomers selected from the group consisting of $C_1$-$C_8$ alkyl acrylates, $C_1$-$C_8$ alkyl methacrylates, $C_1$-$C_4$ alkoxy acrylates, $C_1$-$C_4$ alkoxy methacrylates, and combinations thereof;
   (b) a second polymeric film-former having a second glass transition temperature that is at least 50° C. higher than the first glass transition temperature, wherein the second polymeric film-former comprises an acrylates copolymer having one or more monomers selected from the group consisting of acrylates, alkyl acrylates, methacrylates, alkyl methacrylates, hydroxyesters acrylates, and combinations thereof; and
   (c) a third cross-linked polymeric film-former, wherein the third cross-linked polymeric film-former comprises a taurate crosspolymer; and
wherein the first polymeric film-former and the second polymeric film former are present in the composition in a ratio in the range of from about 2:1 to about 26:1, said ratio based on the total weight of the first and second polymeric film formers in the composition.

2. The mascara or eyeliner composition of claim 1, wherein the first polymeric film-former comprises an acrylates/octyl acrylate copolymer.

3. The mascara or eyeliner composition of claim 2, wherein the acrylates/octyl acrylate copolymer is present in an amount ranging from about 7.5% to about 10% by total weight of said mascara or eyeliner composition.

4. The mascara or eyeliner composition of claim 2, wherein the first polymeric film-former further comprises an ethyl acrylate/methyl methacrylate/methacrylic acid copolymer.

5. The mascara or eyeliner composition of claim 4, wherein the ethyl acrylate/methyl methacrylate/methacrylic acid copolymer is present in an amount ranging from about 1% to about 3% by total weight of said mascara or eyeliner composition.

6. The mascara or eyeliner composition of claim 1, wherein the second polymeric film-former comprises an acrylates/hydroxyesters acrylates copolymer.

7. The mascara or eyeliner composition of claim 6, wherein the acrylates/hydroxyesters acrylates copolymer is present in an amount ranging from about 0.5% to about 1% by total weight of said mascara or eyeliner composition.

8. The mascara or eyeliner composition of claim 1, wherein the second polymeric film-former further comprises a vinyl polymer.

9. The mascara or eyeliner composition of claim 8, wherein the vinyl polymer is present in an amount ranging from about 1% to about 3% by total weight of the mascara or eyeliner composition.

10. The mascara or eyeliner composition of claim 6, wherein the second polymeric film-former comprises a mixture of the acrylates/hydroxyesters acrylates copolymer with polyvinyl acetate.

11. The mascara or eyeliner composition of claim 1, wherein the taurate crosspolymer comprises acryloyl dimethyl taurate monomers and one or more additional monomers selected from the group consisting of styrene, acrylic acid, methacrylic acid, vinyl chloride, vinyl acetate, vinyl pyrrolidone, isoprene, vinyl alcohol, vinyl methylether, chloro-styrene, dialkylamino-styrene, maleic acid, acrylamide, methacrylamide, and combinations thereof.

12. The mascara or eyeliner composition of claim 11, wherein the taurate crosspolymer is an acryloyl dimethyltaurate/vinyl pyrrolidone crosspolymer or an acryloyl dimethyltaurate/beheneth-25 methacrylate crosspolymer.

13. The mascara or eyeliner composition of claim 1, wherein the third cross-linked polymeric film-former is present in an amount ranging from about 0.01% to about 2% by total weight of said mascara or eyeliner composition.

14. The mascara or eyeliner composition of claim 1, which comprises an oil-in-water emulsion, and wherein said first polymeric film-former, said second polymeric film-former, and said third cross-linked polymeric film former are dispersed in an aqueous phase of said oil-in-water emulsion.

15. The mascara or eyeliner composition of claim 14, further comprising one or more waxes in an oil phase of said oil-in-water emulsion.

16. A cosmetic composition comprising:
(a) from about 7.5 wt % to about 10 wt % of an acrylates/octyl acrylate copolymer;
(b) from about 1 wt % to about 3 wt % of an ethyl acrylate/methyl methacrylate/methacrylic acid copolymer;
(c) from about 0.5 wt % to about 1 wt % of an acrylates/hydroxyesters acrylates copolymer;
(d) from about 1 wt % to about 3 wt % of polyvinyl acetate; and
(e) from about 0.1 wt % to about 1 wt % of a cross-linked polymeric film-former which is selected from the group consisting of a taurate crosspolymer.

17. A cosmetic composition consisting essentially of:
(a) from about 7.5 wt % to about 10 wt % of an acrylates/octyl acrylate copolymer;
(b) from about 1 wt % to about 3 wt % of an ethyl acrylate/methyl methacrylate/methacrylic acid copolymer;
(c) from about 0.5 wt % to about 1 wt % of an acrylates/hydroxyesters acrylates copolymer;
(d) from about 1 wt % to about 3 wt % of polyvinyl acetate; and
(e) from about 0.1 wt % to about 1 wt % of a cross-linked polymeric film-former which is a taurate crosspolymer.

* * * * *